United States Patent
Guvendiren et al.

(10) Patent No.: US 12,121,632 B2
(45) Date of Patent: Oct. 22, 2024

(54) ADDITIVE MANUFACTURING OF CELL-LADEN FUNCTIONAL HYDROGEL AND LIVE CELL CONSTRUCTS

(71) Applicant: New Jersey Institute of Technology, Newark, NJ (US)

(72) Inventors: Murat Guvendiren, Metuchen, NJ (US); Shen Ji, Kearny, NJ (US); Alperen Abaci, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 18/370,939

(22) Filed: Sep. 21, 2023

(65) Prior Publication Data

US 2024/0009354 A1 Jan. 11, 2024

Related U.S. Application Data

(60) Division of application No. 17/588,998, filed on Jan. 31, 2022, now Pat. No. 11,806,444, which is a
(Continued)

(51) Int. Cl.
*B33Y 10/00* (2015.01)
*A61L 27/20* (2006.01)
(Continued)

(52) U.S. Cl.
CPC ............ *A61L 27/52* (2013.01); *A61L 27/20* (2013.01); *A61L 27/38* (2013.01); *A61L 27/507* (2013.01);
(Continued)

(58) Field of Classification Search
None
See application file for complete search history.

(56) References Cited

U.S. PATENT DOCUMENTS 7,766,641 B2    8/2010  Silverbrook
10,759,107 B2 * 9/2020  Batchelder ............ B33Y 50/02
(Continued)

FOREIGN PATENT DOCUMENTS

CN      107998449 A         5/2018
WO      2010048281 A1       4/2010
WO      WO-2018-112480 A1 * 6/2018

OTHER PUBLICATIONS

Ji S, Guvendiren M. Recent advances in bioink design for 3D bioprinting of tissues and organs. Frontiers in bioengineering and biotechnology. Apr. 5, 2017;5:23.
(Continued)

*Primary Examiner* — Mohammad M Ameen
(74) *Attorney, Agent, or Firm* — Lerner David LLP

(57) ABSTRACT

Disclosed is a new 3D bioprinting method of soft polymeric material such as a hydrogel or elastomer and/or cells for scaffolds or devices with structures. The method utilizes in one aspect extrusion based printing of polymer solutions, hydrogels and cells referred as direct ink writing (DIW) or BioPlotting that is modified to offer break-through advantages. The method may utilize sequential printing of a photocurable polymer solution or matrix material, and a functional hydrogel and/or cells. Printing within or inside of a viscous non-cured layer is accomplished by printing cells directly into the functional hydrogel. The viscous layer does not need to be shear thinning and thus allows use of a wide variety of bioinks never before allowed because of shear thinning and recovery requirement of commonly utilized extrusion based embedded bioprinting approach. Complex printing patterns never before allowed for bioinks are now possible utilizing this new printing method.

20 Claims, 2 Drawing Sheets

Related U.S. Application Data continuation-in-part of application No. 16/533,216, filed on Aug. 6, 2019, now Pat. No. 11,491,702.

(60) Provisional application No. 63/146,307, filed on Feb. 5, 2021, provisional application No. 62/715,869, filed on Aug. 8, 2018.

(51) Int. Cl.
| | |
|---|---|
| *A61L 27/38* | (2006.01) |
| *A61L 27/50* | (2006.01) |
| *A61L 27/52* | (2006.01) |
| *A61L 27/56* | (2006.01) |
| *B29C 64/106* | (2017.01) |
| *B29C 64/40* | (2017.01) |
| *B29K 105/00* | (2006.01) |
| *B29L 31/00* | (2006.01) |
| *B33Y 70/00* | (2020.01) |

(52) U.S. Cl.
CPC ............ *A61L 27/56* (2013.01); *B29C 64/106* (2017.08); *B29C 64/40* (2017.08); *B33Y 10/00* (2014.12); *A61L 2420/08* (2013.01); *B29K 2105/0061* (2013.01); *B29L 2031/753* (2013.01); *B33Y 70/00* (2014.12)

(56) References Cited

U.S. PATENT DOCUMENTS

| | | | |
|---|---|---|---|
| 2003/0099737 A1 | 5/2003 | Eldridge et al. | |
| 2004/0237822 A1 | 12/2004 | Boland et al. | |
| 2006/0237880 A1 | 10/2006 | Wicker et al. | |
| 2010/0092796 A1 | 4/2010 | Cao et al. | |
| 2015/0024169 A1 | 1/2015 | Martin | |
| 2015/0037445 A1* | 2/2015 | Murphy | C12M 33/12 425/131.1 |
| 2015/0084232 A1* | 3/2015 | Rutz | A61L 27/18 435/325 |
| 2015/0147421 A1* | 5/2015 | Te | B29C 64/40 118/302 |
| 2015/0202348 A1 | 7/2015 | Dvir et al. | |
| 2016/0167312 A1 | 6/2016 | Feinberg et al. | |
| 2017/0197371 A1 | 7/2017 | Fetfatsidis et al. | |
| 2017/0198275 A1* | 7/2017 | Lee | C12Q 1/02 |
| 2017/0218228 A1 | 8/2017 | Jose et al. | |
| 2018/0104895 A1 | 4/2018 | Slaczka et al. | |
| 2018/0243988 A1 | 8/2018 | Lewicki | |
| 2018/0304361 A1 | 10/2018 | Gibson et al. | |

OTHER PUBLICATIONS

Murphy SV, Atala A. 3D bioprinting of tissues and organs. Nature biotechnology. Aug. 2014;32(8):773-85.

Miller JS, Stevens KR, Yang MT, Baker BM, Nguyen DH, Cohen DM, Toro E, Chen AA, Galie PA, Yu X, Chaturvedi R. Rapid casting of patterned vascular networks for perfusable engineered three-dimensional tissues. Nature materials. Sep. 2012;11(9):768-74.

Kolesky DB, Truby RL, Gladman AS, Busbee TA, Homan KA, Lewis Ja. 3D bioprinting of vascularized, heterogeneous cell-laden tissue constructs. Advanced materials. May 2014;26(19):3124-30.

Liaw CY, Guvendiren M. Current and emerging applications of 3D printing in medicine. Biofabrication. Jun. 7, 2017;9(2):024102.

Wu W, DeConinck A, Lewis JA. Omnidirectional printing of 3D microvascular networks. Advanced materials. Jun. 24, 2011;23(24):H178-83.

Hinton TJ, Jallerat Q, Palchesko RN, Park JH, Grodzicki MS, Shue HJ, Ramadan MH, Hudson AR, Feinberg AW. Three-dimensional printing of complex biological structures by freeform reversible embedding of suspended hydrogels. Science advances. Oct. 1, 2015;1(9):e1500758.

O'Bryan CS, Bhattacharjee T, Hart S, Kabb CP, Schulze KD, Chilakala I, Sumerlin BS, Sawyer WG, Angelini TE. Self-assembled micro-organogels for 3D printing silicone structures. Science advances. May 1, 2017;3(5):e1602800.

Highley CB, Rodell CB, Burdick JA. Direct 3D printing of shear-thinning hydrogels into self-healing hydrogels. Advanced Materials. Sep. 2015;27(34):5075-9.

Kolesky DB, Homan KA, Skylar-Scott MA, Lewis JA. Three-dimensional bioprinting of thick vascularized tissues. Proceedings of the national academy of sciences. Mar. 22, 2016;113(12):3179-84.

Jia W, Gungor-Ozkerim PS, Zhang YS, Yue K, Zhu K, Liu W, Pi Q, Byambaa B, Dokmeci MR, Shin SR, Khademhosseini A. Direct 3D bioprinting of perfusable vascular constructs using a blend bioink. Biomaterials. Nov. 1, 2016;106:58-68.

Hinton TJ, Hudson A, Pusch K, Lee A, Feinberg Aw. 3D printing PDMS elastomer in a hydrophilic support bath via freeform reversible embedding. ACS biomaterials science & engineering. Oct. 10, 2016;2(10):1781-6.

Hasany, Masoud et al., "Synthesis, properties, and biomedical applications of alginate methacrylate (ALMA)-based hydrogels: Current advances and challenges," Applied MaterialsToday 24 (Sep. 2021): 101150. 20 pgs.

* cited by examiner

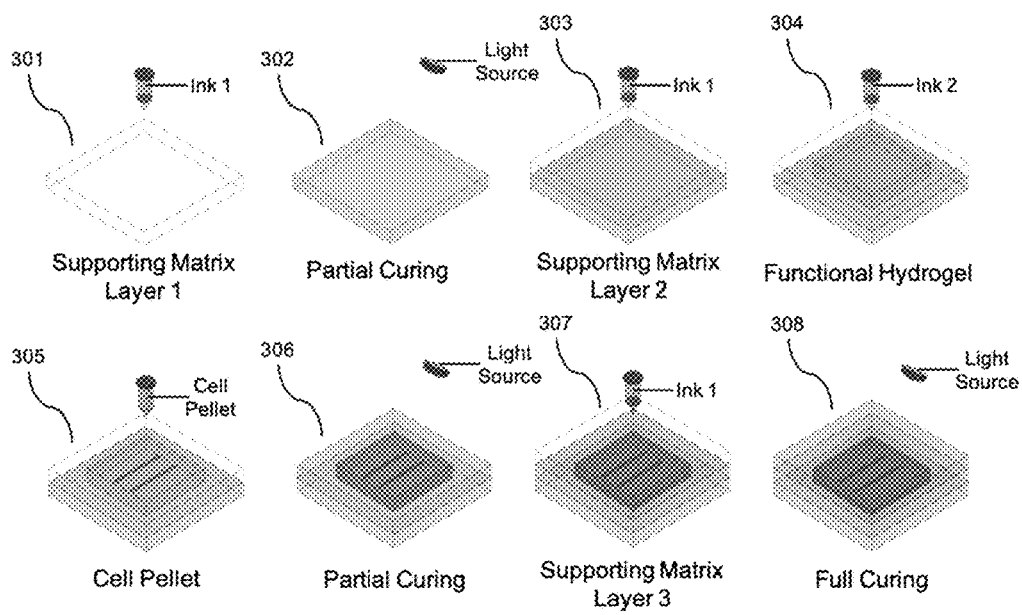
Figure 3.
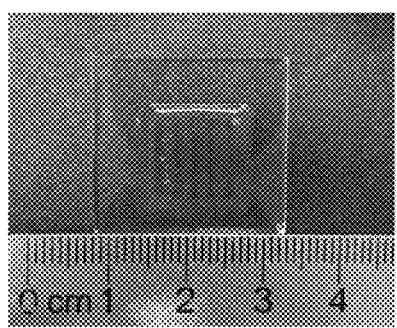 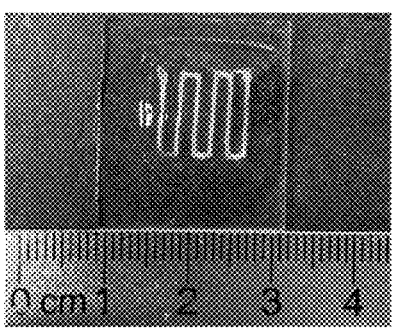 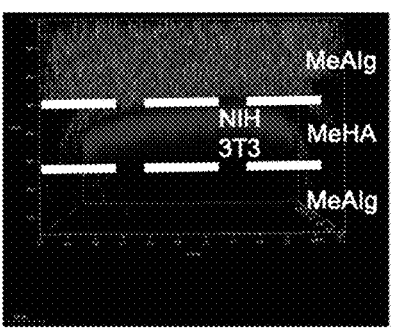
Figures 4A-4C.

ADDITIVE MANUFACTURING OF CELL-LADEN FUNCTIONAL HYDROGEL AND LIVE CELL CONSTRUCTS

CROSS-REFERENCE TO RELATED APPLICATIONS

This application is a divisional of U.S. application Ser. No. 17/588,998, filed on Jan. 31, 2022, which is a continuation in part of pending application U.S. Non-Provisional patent application Ser. No. 16/533,216 filed on Aug. 6, 2019, which claims the benefits of the filing date of U.S. Provisional Patent Application No. 63/146,307, filed Feb. 5, 2021, the disclosures of which are hereby incorporated herein by reference.

FIELD OF THE DISCLOSURE

The present disclosure relates to a new method of 3D bioprinting. In particular, the present disclosure relates to additive manufacturing of 3D scaffolds and devices, and bioprinting of functional cell-laden structures where cells are printed inside and embedded in a viscous non-cured layer using a wider range of printable and biocompatible materials due to reduced shear stress in printing.

BACKGROUND

The technology of 3D bioprinting has been developed as a promising technology in a wide variety of biomedical applications. However, the successful implementation of bioprinting is still heavily restricted by the relatively narrow range of printable and biocompatible materials. It is still a technical challenge to create cell only tissues, cell-laden hydrogel scaffolds, vascularized scaffolds or hydrogels with embedded channels for vascularization, and soft microfluidic devices from elastomers or hydrogels. For example, material requirements for printability for conventional printing methods significantly limit the type of material available for these conventional printing methods. Required is a fast and simple approach to create cell-only tissue, cell-laden hydrogel scaffolds and channels within soft systems such as hydrogels and elastomers.

One such approach is extrusion-based freeform printing allowing bioprinting of soft hydrogels and/or cells within a support bath. In this approach, the support bath material required to have shear thinning and recovery behavior to allow printing needle to move freely within the bath material. Thus, these freeform printing approaches require development of special materials and are not applicable to a wide range of materials. In addition, these 3D bioprinting techniques require the use of excess material as well as modification of the biorprinting device and software, which increases the cost of the fabrication. The term bioink generally refers to materials composed of living cells that can be used for 3D printing of complex tissue models. Bioinks are materials that mimic an extracellular matrix environment to support high cell viability and potentially to support the adhesion, proliferation, and differentiation of living cells.

Additive manufacturing, commonly known as 3D printing, has become increasingly popular over recent years. Additive manufacturing refers generally to processes used to manufacture a three-dimensional object in which successive layers of material are formed under computer control to create a 3D construct or a device. One application of additive manufacturing allows fabrication of complex 3D structures from a patient's own medical image, which is not possible with conventional fabrication techniques. Additive manufacturing of biological materials, i.e., bioinks (cells, cell-laden hydrogels, extracellular matrix materials, and their various combinations), is referred as bioprinting. Extrusion-based bioprinting, usually referred as direct ink writing (DIW), is one of the mostly utilized 3D printing approaches for tissue and organ printing studies.

Recent focus in the biomanufacturing field is to fabricate 3D tissue and organ mimetics, such as in the form of organ-on-a-chip devices, for disease modeling and drug development and screening, to human-scale scaffolds for tissue regeneration. This requires bioprinting of cell-laden functional hydrogels, i.e., hydrogels that allow tethering of bioactive cues to control cell function, and cells alone (in the form of cellular aggregates and/or spheroids) to create living tissues. Accordingly, there still remains a need for a new method of making 3D scaffolds and devices without the above drawbacks.

SUMMARY

The present disclosure avoids the drawbacks of freeform 3D printing methods and provides many other advantages on printing self-supporting polymeric materials, hydrogels, and cells. No additional processing steps or requirements are needed for the photocurable bioinks, including shear-thinning and shear-recovery behavior. A reservoir of support materials, for example, a support bath, is eliminated as compared to commonly utilized extrusion-based free form printing approaches. The present approach is applicable to commercially available bioprinters, and does not require hardware or software modifications.

In one aspect, a method for making a 3D scaffold or a device could include the step of printing a first photocurable polymer matrix material layer, a second photocurable polymer matrix material after partial photocuring of the first layer, and a functional hydrogel, wherein the functional hydrogel is printed or embedded within the second photocurable matrix material prior to partial curing.

In another aspect, a method for making a 3D scaffold or a device could include the step of printing a first functional hydrogel layer followed by partial curing, a second functional hydrogel layer, and cells wherein the cells are printed into the second functional hydrogel layer prior to partial curing. In another embodiment, a method for making a 3D scaffold or a device could include the step of printing a first photocurable polymer matrix material layer following by partial curing, a second photocurable polymer matrix material, a functional hydrogel, and cells, wherein the functional hydrogel is printed or embedded in the supporting hydrogel, and the cells are printed into the functional hydrogel.

In addition, a method could include fabrication of polymeric scaffolds/devices with embedded structures by printing a sacrificial polymer/hydrogel directly within the interface of the photocurable functional cell-laden hydrogel layer, or vice versa. The printing may be sequential.

In another aspect, a cell-laden matrix hydrogel could be printed within or inside a sacrificial hydrogel or support by switching the order of the printing process. In another embodiment, the functional hydrogel could be printed within a support hydrogel first, and then the cells. Aggregates or spheroids can then be printed directly within this embedded matrix hydrogel. In this approach, it was found that printing within a material allows such printing without shear-thinning and recovery behavior. This technical feature by printing bioinks directly inside an uncured material significantly expands the available printable inks. This approach targets photocurable bioinks, however, it may be applied to a wide variety of any commercially available photocurable bioinks. This is a huge advantage as this material can be a support material or a functional hydrogel. The printed material can be any type of photocurable bioink—cell-laden hydrogel, sacrificial hydrogel, or cells alone.

Depending on the implementation, the printing method may include the following steps. First, printing a layer (support or functional hydrogel) and curing the layer by exposing it to light briefly to allow self-support. This first step may be repeated as many times as desired depending on the purpose of the construct. Next, a layer is printed and not cured. Then printing is done within this viscous non-cured layer.

The viscous layer does not need to be shear thinning. This ability to print bioink or any type of photocurable bioink—cell-laden hydrogel, sacrificial hydrogel, or cells alone in such a manner is a new method never before known in the industry.

In this way, one can print a functional hydrogel within a support hydrogel, and then print directly cells within the functional hydrogel. This method is a significant advancement over conventional methods that need functional hydrogels to control cellular behavior. Also the complexity in patterns for printing using this method is increased. For example, cells may be printed within a functional hydrogel in a complex printing pattern or structure within another material. Note that this type of bioprinting is not known in the art.

Some examples of complex patterns or structures include but are not limited to the designs shown in the Figures. Additional complex patterns or structures, include but are not limited to, and are illustrated in the various patterns and structures found in the human anatomy such as shapes of bone structures, organs, tissues, ligaments, and the like and any combination thereof.

The above objects and advantages are met by the presently disclosed method and apparatus. In addition the above and yet other objects and advantages of the present invention will become apparent from the hereinafter-set forth Brief Description of the Drawings, Detailed Description of the Invention, and claims appended herewith. These features and other features are described and shown in the following drawings and detailed description.

Furthermore, any combination and/or permutation of the embodiments are envisioned. Again, other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disclosed method to make a device using 3D printing and associated systems and methods, reference is made to the accompanying figures, wherein:

FIG. 3 shows views outlining one embodiment of a printing method to print a functional hydrogel embedded in a 3D supporting hydrogel and print cells into a functional hydrogel; and FIGS. 4A-4C show 3D printed structures with the embodiments of FIGS. 1, 2, and 3, respectively. A top view of a functional hydrogel printed with different thickness values (FIG. 4A), a top view of cells directly printed into a functional hydrogel (FIG. 4B), and a confocal microscope image of cells and functional hydrogel within a supporting hydrogel (FIG. 4C) is shown.

DETAILED DESCRIPTION

Exemplary embodiments are directed to 3D printing of soft polymeric scaffolds or devices. It should be understood that embodiments could generally be applied to other scaffolds or devices, including but not limited to cell only tissues, cell-laden hydrogel devices, hydrogel scaffolds with embedded cellular constructs, hydrogel devices with embedded cell-laden hydrogel constructs.

In one embodiment, a method is disclosed for 3D printing of soft polymeric (hydrogel or elastomer) scaffolds or devices with embedded structures. The method could utilize extrusion-based printing of polymer solutions usually referred as direct ink writing (DIW) or BioPlotting, and requires sequential printing of a photocurable polymer solution referred herein as a matrix material and a functional hydrogel in one embodiment. The matrix material may be a supporting layer or a supporting structure. In another embodiment, the method could require sequential printing of a functional hydrogel layer and cells. In another embodiment, the method could require sequential printing of a matrix/support material, a functional hydrogel layer, and cells.

In one embodiment, the fabrication process starts with 3D printing several layers of matrix material. Matrix material could be any photocurable hydrogel ink. The ink is not required to show shear thinning behavior or self-support itself after printing, which allows the use of a wide range of materials. After printing each layer, the printed matrix solution is exposed to light for a very short time (~15 s) to partially cure the printed layer. This method allows the matrix hydrogel to self-support itself. When the desired matrix material height (thickness) is reached, one additional layer of matrix material is printed but not exposed to light. A functional hydrogel and/or cells are directly printed within this matrix layer.

This non-crosslinked matrix layer supports the printed functional hydrogel and/or the cells. The system is then exposed to light to partially crosslink the matrix layer. Then another layer of matrix material is printed followed by light exposure. This process is repeated as needed to reach the final desired scaffold/device thickness.

Figure 1:
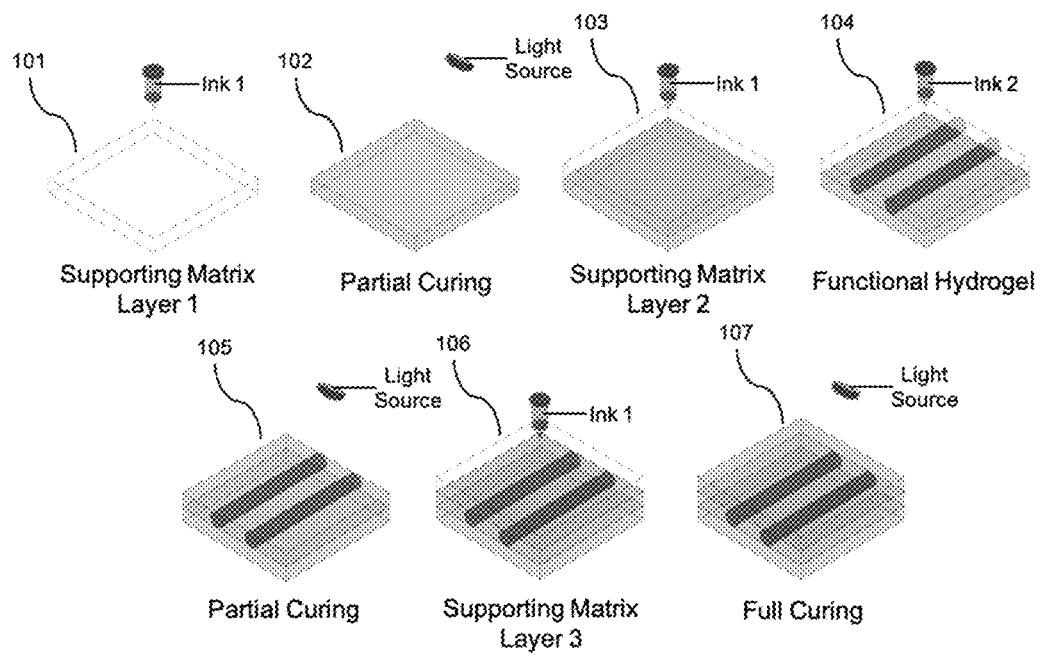
FIG. 1 shows views outlining one embodiment of a printing method to print a functional hydrogel embedded in a 3D supporting hydrogel.

FIG. 1 shows views outlining one embodiment of a printing method. The method involves 3D printing several layers of a supporting matrix material and a functional hydrogel within the matrix. A dual print-head with a light source is utilized in the method. A first supporting matrix layer 101 is printed using a supporting matrix ink (Ink 1, as shown in FIG. 1) and partially cured for a certain period of time to form a partially cured supporting matrix layer 102. In one embodiment, the first supporting matrix layer is partially cured using a light source for around 15 seconds. It will be understood that the partial curing time could vary depending on several factors, such as the material. A second supporting matrix layer 103 is printed on the first supporting matrix layer, which has been partially cured. A functional hydrogel (Ink 2, as shown in FIG. 1) 104 is printed within the second supporting matrix layer. In one embodiment, the functional hydrogel is printed within the second supporting matrix layer before the second supporting matrix layer is exposed to light. The second supporting matrix layer is sized to support the functional hydrogel. The first supporting matrix layer, the second supporting matrix layer, and/or the functional hydrogel are partially cured as shown in 105 for a certain period of time to crosslink the second layer. Depending on the embodiment, only the second matrix layer is exposed to light in this step. A third supporting matrix layer 106 is printed on the second supporting matrix layer. The first supporting matrix layer, the second supporting matrix layer, the functional hydrogel, and/or the third supporting matrix layer are fully cured as shown in 107 for a certain period of time to crosslink the printed structure. In one embodiment, only the third matrix layer is exposed to light in this step.

A 3D printed construct is formed, which includes the first supporting matrix layer, the second supporting matrix layer, the functional hydrogel, and the third supporting matrix layer in this embodiment. It will be understood that while only three matrix layers and one functional layer are shown in FIG. 1, the number of matrix layers and functional layers could vary. Depending on the implementation, the supporting matrix has no biological function besides supporting the printed structure. The supporting matrix can be permanent or easily removed after a user-defined time depending on the selection of the material.

Figure 2:
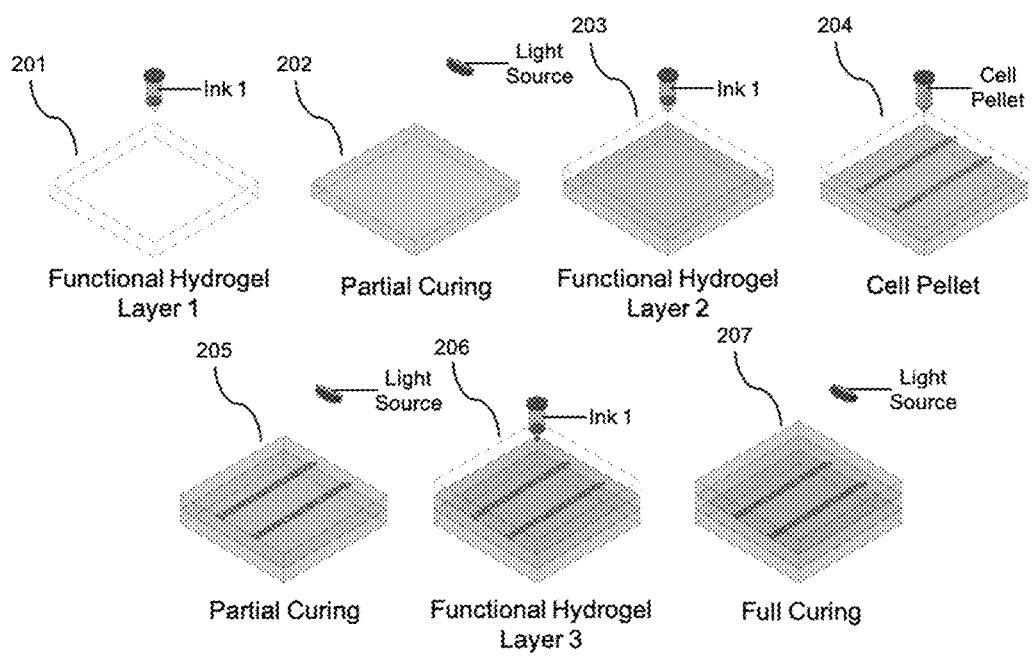
FIG. 2 shows views outlining one embodiment of a printing method to print cells directly into a functional hydrogel.

FIG. 2 shows views outlining another embodiment of a printing method. The method involves 3D printing several layers of a functional hydrogel and a cell pellet within the matrix. A dual print-head with a light source is utilized in the method. It is also within the scope of this invention to use a one head printer by changing the ink after each layer is printed. A first functional matrix layer 201 is printed using a functional hydrogel ink (Ink 1, as shown in FIG. 2) and partially cured for a certain period of time to form a partially cured matrix layer 202.

Depending on the implementation, the first matrix layer is partially cured using a light source for around 5 seconds. The partial curing time could vary depending on several factors, such as the material. A second functional matrix layer 203 is printed on the first functional matrix layer. A cell pellet loaded into a syringe (cell pellet, as shown in FIG. 2) 204 is printed within the second functional matrix layer. The second functional matrix layer is sized to support the cells printed within the functional hydrogel. The second functional matrix layer is partially cured as shown in 205 for a certain period of time to crosslink the second layer. A third functional matrix layer 206 is printed on the second functional matrix layer. The first functional matrix layer, the second functional matrix layer, and/or the third functional matrix layer are fully cured as shown in 207 for a certain period of time to crosslink the printed structure.

A 3D printed construct is formed, which includes the first functional matrix layer, the second functional matrix layer, the cell pellet, and the third functional matrix layer in this embodiment. It will be understood that while only three matrix layers and one cell layer are shown in FIG. 2, the number of matrix layers and cell layers could vary. As defined in this specification the use of the term functional hydrogel or functional layer refers to a hydrogel or material layer that can be easily functionalized with bioactive cues to control cell behavior.

FIG. 3 shows views outlining another embodiment of a printing method. The method involves 3D printing several layers of a supporting matrix material, a functional hydrogel embedded in the supporting matrix, and a cell pellet within the functional material. A triple print-head with a light source is utilized in the method. Again, it is within the scope of this invention also to use a one head printer by changing the ink after each layer is printed.

A first supporting matrix layer 301 is printed using a supporting hydrogel ink (Ink 1, as shown in FIG. 3) and partially cured for a certain period of time to form a partially cured matrix layer 302. In one embodiment, the first matrix layer is partially cured using a light source for around 15 seconds. Again, the partial curing time could vary depending on several factors, such as the material. A second supporting matrix layer 303 is printed on the first supporting matrix layer. A functional hydrogel (Ink 2, as shown in FIG. 3) 304 is printed within, or again inside or embedded inside the second supporting matrix layer. A cell pellet loaded into a syringe (cell pellet, as shown in FIG. 3) 305 is printed within the functional matrix layer. In one embodiment, the cell pellet is printed within the functional matrix layer before the second matrix layer is exposed to light. The second supporting matrix layer is sized to support the functional hydrogel layer and cells printed within the functional hydrogel. The first supporting matrix layer, the second supporting matrix layer, and/or the functional hydrogel layer are partially cured as shown in 306 for a certain period of time to crosslink the second layer. A third supporting matrix layer 307 is printed on the second matrix layer. The first supporting matrix layer, the second supporting matrix layer, the functional hydrogel layer, and/or the third supporting matrix layer are fully cured as shown in 308 for a certain period of time to crosslink the printed structure.

A 3D printed construct is formed, which includes the first supporting matrix layer, the second supporting matrix layer, the functional hydrogel layer, the cell pellet, and the third supporting matrix layer in this embodiment. It will be understood that while only three supporting matrix layers, one functional hydrogel layer, and one cell layer are shown in FIG. 3, the number of supporting/functional matrix layers and cell layers could vary.

The materials and the methods of the present disclosure used in one embodiment for a hydrogel scaffold and device will be described below. While the embodiment discusses the use of specific compounds and materials, it is understood that the present disclosure could employ other suitable materials. Similar quantities or measurements may be substituted without altering the method embodied herein.

Depending on the implementation, methacrylated hyaluronic acid (MeHA) hydrogel may be used as a functional hydrogel matrix ink and methacrylated alginate (MeAlg) hydrogel may be used as a supporting matrix ink. Ink formulations were prepared by dissolving MeHA or MeAlg in PBS at different concentrations in the presence of a photoinitiator, lithium phenyl-2,4,6-trimethylbenzoylphosphinate (LAP), for blue light crosslinking. A blue light initiator was used as the 3D printer has a built in blue light source. Several ink formulations were developed by varying the MeHA or MeAlg concentration. One of the suitable bioink formulations was 10 wt. % MeHA and/or 9 wt. % MeAlg, allowing extrusion-based printing of the solution. Using the disclosure of the new printing method, struts (individual lines) as small as 100-microns in diameter were able to be generated.

A cell pellet without any additional carriers, such as another hydrogel or a cell culture media, was directly printed into a functional hydrogel, as shown in FIG. 2 and FIG. 3. To extrude cells, a syringe pump printhead was used, instead of extruding them with pneumatic pressure. Other suitable devices could be employed as well adding to the flexibility of the new printing method. In one embodiment, NIH 3T3 cells were utilized as the print 3D structures; however, any type of cells can be utilized with this method.

The approach is versatile and enables printing of a functional hydrogel with varying sizes within a supporting matrix, and printing of cells directly into a functional hydrogel. FIGS. 4A-4C demonstrate some of the corresponding 3D printed structures.

FIG. 4A illustrates optimizing dimensions of functional hydrogel (MeHA) printed within the supporting matrix (MeAlg). FIG. 4B illustrates printing cells (NIH 3T3) directly within a functional hydrogel (MeHA). FIG. 4C illustrates printing functional hydrogel (MeHA) within a supporting matrix (MeAlg) and printing cells (NIH 3T3) within the functional hydrogel layer.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A method for making a 3D scaffold or a device, the method comprising the steps of:
    first, printing a support hydrogel layer or a photocurable functional hydrogel layer that are photocurable and viscous;
    second, curing either layer to form a self-support structure by exposing either layer to a light source;
    third, repeating the printing and curing steps to achieve a desired thickness of the self-support structure;
    fourth, printing and leaving an uncured photocurable layer that is a viscous layer with no shear thinning properties; and
    fifth, printing a bioink inside the viscous layer.

2. The method of claim 1, wherein the bioink contains living cells.

3. The method of claim 1, wherein the photocurable layer is another functional layer.

4. The method of claim 1, wherein the functional layer is printed inside the support layer.

5. The method of claim 1, further includes a step of curing the viscous layer with the bioink inside the viscous layer.

6. The method of claim 1, further includes a step of forming complex patterns or structures with the bioink.

7. The method of claim 1, wherein the complex patterns or structures are selected from a group consisting of shapes of bone structures, organs, tissues, ligaments, and any combination thereof.

8. A method for making a 3D scaffold or a device, the method comprising the steps of:
    printing a support hydrogel layer or a photocurable functional hydrogel layer that are photocurable and viscous;
    partially curing either layer to form a self-support structure by exposing either layer to a light source;
    repeating the printing and curing steps to achieve a desired thickness of the self-support structure; and
    printing a bioink inside the viscous layer.

9. The method of claim 8, wherein the partially curing by the light source is for an exposure duration of less than or equal to 15 seconds.

10. The method of claim 8 wherein the bioink contains a plurality of NIH 3T3 cells.

11. The method of claim 10 further includes extruding by using a syringe pump to deliver the plurality of NIH 3T3 cells into the functional hydrogel layer.

12. The method of claim 8, further includes printing cells directly within the functional hydrogel.

13. The method of claim 12, wherein the printing cells directly within the functional hydrogel further includes using a cell pellet to deliver the cells.

14. The method of claim 8, wherein the uncured photocurable layer is a methacrylated hyaluronic acid (MeHA) hydrogel.

15. The method of claim 8, wherein the support hydrogel layer is a methacrylated alginate (MeAlg) hydrogel.

16. A method for making a 3D scaffold or a device, the method comprising the steps of:
    printing a support hydrogel layer that is photocurable and viscous;
    partially curing the support hydrogel layer by exposing the layer to a light source;
    printing a bioink within the support layer wherein the bioink contains cells; and
    fully curing the support hydrogel layer and the bioink with the light source.

17. The method of claim 16, wherein the support hydrogel layer is sized to support the cells printed within the hydrogel layer.

18. The method of claim 17 wherein the support layer is partially cured for 15 seconds.

19. The method of claim 16, further including using a syringe loaded with a cell pellet to deliver the cells within the support layer.

20. The method of claim 16, wherein the support layer is partially cured for 5 seconds.

* * * * *